(12) United States Patent
Haddadi

(10) Patent No.: US 9,706,909 B2
(45) Date of Patent: Jul. 18, 2017

(54) APPARATUS FOR DETERMINING THE DOMINANT EYE

(71) Applicant: ESSILOR INTERNATIONAL (COMPAGNIE GENERALE D'OPTIQUE), Charenton-le-Pont (FR)

(72) Inventor: Ahmed Haddadi, Charenton-le-Pont (FR)

(73) Assignee: ESSILOR INTERNATIONAL (COMPAGNIE GENERALE D'OPTIQUE), Charenton-le-Pont ( * ) Notice: Subject to any disclaimer, the term of this patent is extended or adjusted under 35 U.S.C. 154(b) by 0 days.

(21) Appl. No.: 14/778,241

(22) PCT Filed: Mar. 6, 2014

(86) PCT No.: PCT/FR2014/050514
§ 371 (c)(1),
(2) Date: Sep. 18, 2015

(87) PCT Pub. No.: WO2014/147317
PCT Pub. Date: Sep. 25, 2014

(65) Prior Publication Data
US 2016/0287069 A1 Oct. 6, 2016

(30) Foreign Application Priority Data
Mar. 21, 2013 (FR) .................................. 13 52519

(51) Int. Cl.
A61B 3/10 (2006.01)
A61B 3/02 (2006.01)
(Continued)

(52) U.S. Cl.
CPC .............. *A61B 3/02* (2013.01); *A61B 3/0025* (2013.01); *A61B 3/0058* (2013.01);
(Continued)

(58) Field of Classification Search
CPC .......... A61B 3/0091; A61B 3/111; A61B 3/00
(Continued)

(56) References Cited

U.S. PATENT DOCUMENTS

2014/0016090 A1* 1/2014 Bonnin .................... A61B 3/10
351/204
2014/0098343 A1 4/2014 Haddadi

FOREIGN PATENT DOCUMENTS

FR 2 972 339 A1 9/2012
FR 2 972 911 A1 9/2012
(Continued)

OTHER PUBLICATIONS

International Search Report, dated Jun. 16, 2014, from corresponding PCT application.
(Continued)

Primary Examiner — Hung Dang
(74) Attorney, Agent, or Firm — Young & Thompson

(57) ABSTRACT

An apparatus for implementing a method for determining the dominant eye of a spectacle wearer (1), includes a target (2), an element (3, 4) for occulting at least one eye, and a sighting device (5, 50) equipped with an optical window (6). The principal feature of the apparatus is that the sighting device (5, 50) includes an electronic sensor making it possible to identify the direction of movement of the sighting device (5, 50), during the method during various steps of viewing the target (2).

20 Claims, 2 Drawing Sheets

(51) Int. Cl.
*A61B 3/113* (2006.01)
*A61B 3/00* (2006.01)
*A61B 3/14* (2006.01)

(52) U.S. Cl.
CPC ............ *A61B 3/0075* (2013.01); *A61B 3/113* (2013.01); *A61B 3/14* (2013.01)

(58) Field of Classification Search
USPC .................................... 351/204, 246, 200
See application file for complete search history.

(56) References Cited

FOREIGN PATENT DOCUMENTS

| WO | 01/47463 A1 | 7/2001 |
|----|-------------|--------|
| WO | 2006/106248 A1 | 10/2006 |

OTHER PUBLICATIONS

FR Search Report, dated Nov. 27, 2013, from corresponding FR application.

* cited by examiner

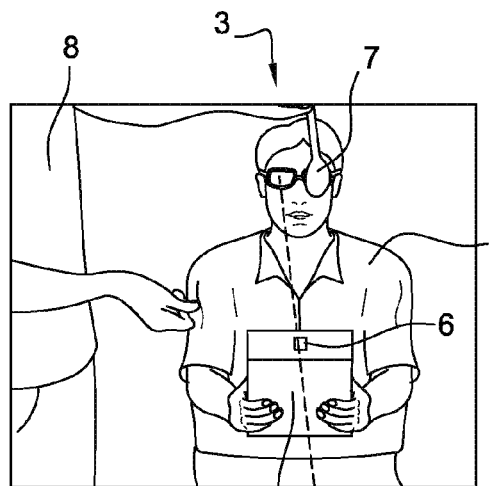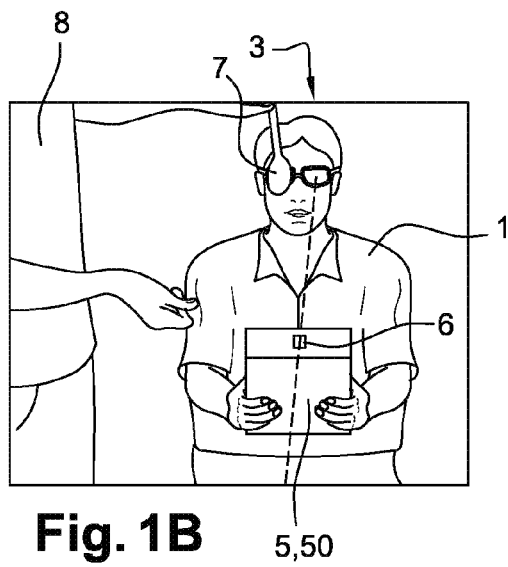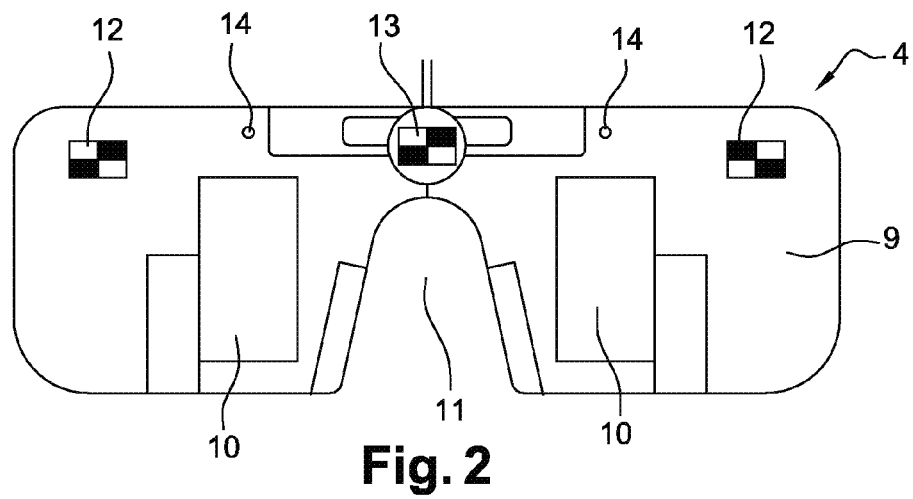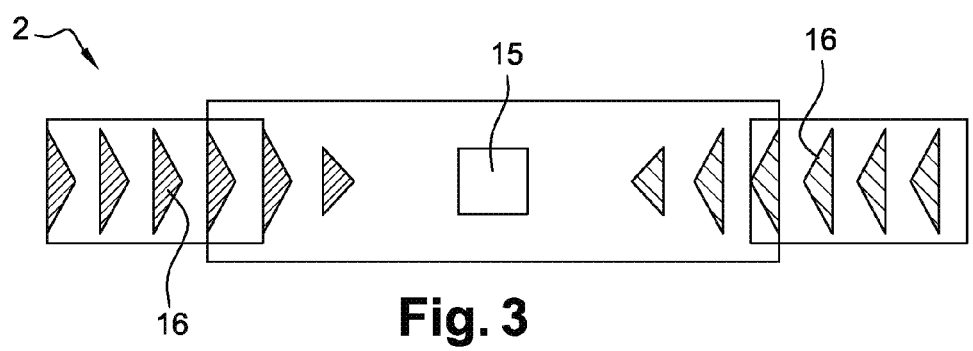

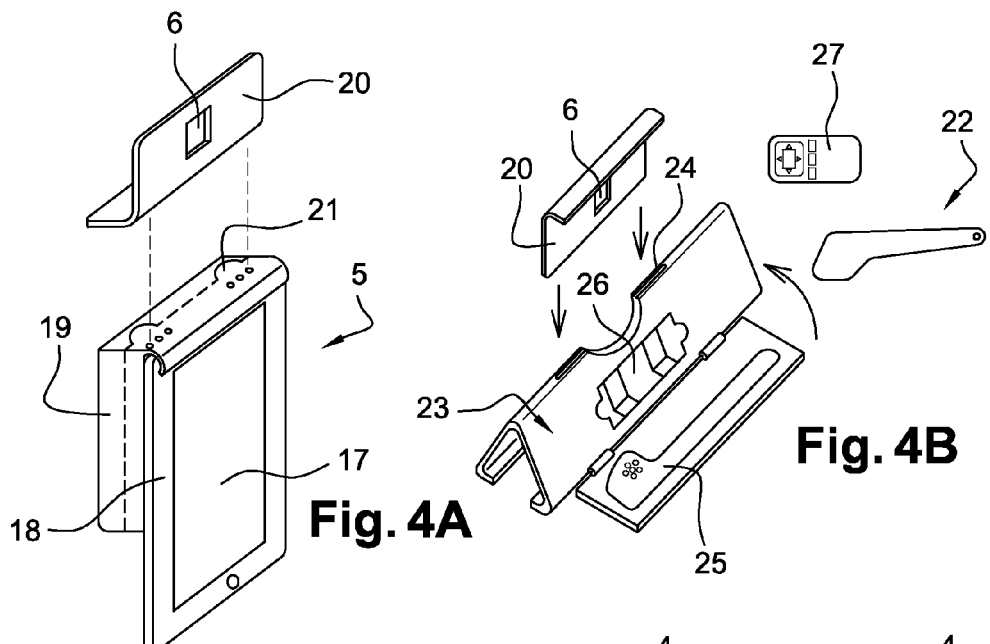
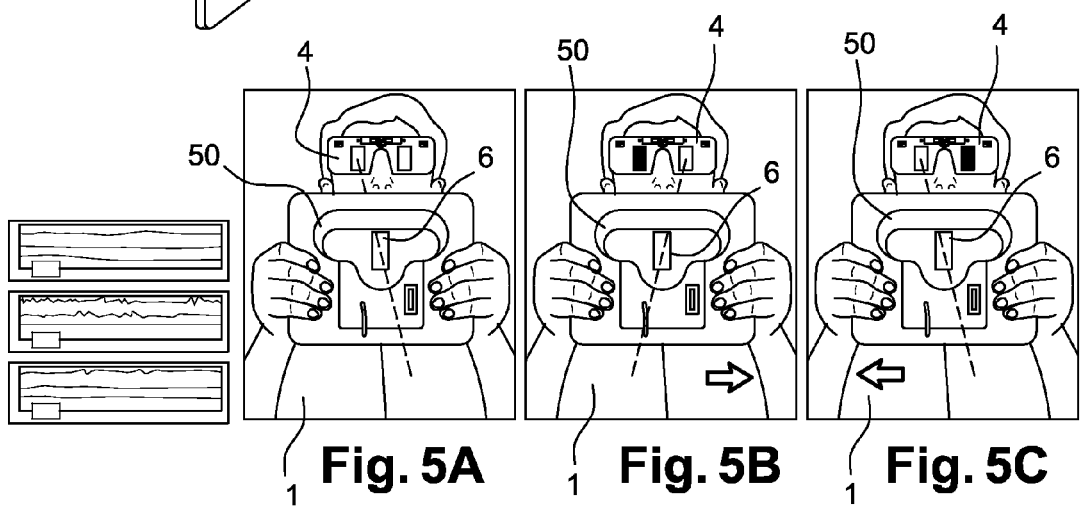
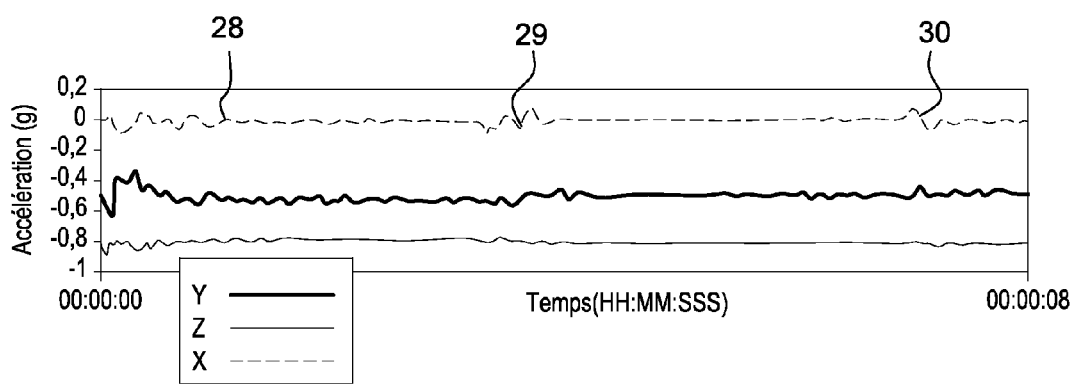

APPARATUS FOR DETERMINING THE DOMINANT EYE

The invention relates to an apparatus for determining the dominant eye. This invention relates to the field of personalization of corrective glasses, and more specifically to an apparatus able to determine the ocular dominance parameter, also referred to as the "dominant eye", of a spectacle wearer. The invention also relates to a method for measuring this dominant eye by means of said apparatus.

Such methods and apparatus already exist. Mention may for example be made of patent FR2972339, which describes a method for determining the dominant eye of a spectacle wearer, by means of a sighting device equipped with an optical window, and a system for acquiring images. The principle of such a method is based on the wearer viewing a target through said optical window, and on acquisition of an image showing the face of said wearer and the position of the optical window while he is viewing the target. Processing of the image obtained makes it possible to determine without ambiguity the dominant eye of the individual. The sighting device is embodied by a manual tablet, equipped with locating markers and an optical window. This method is ergonomic and practical for the wearer since the operation of viewing the target is carried out with both eyes open, said method being solid and rigorous because the information obtained regarding the dominant eye is unequivocal and delivered directly to said wearer without the latter having to make the slightest bit of effort. However, one drawback of this type of method is that it implements a bulky apparatus, which it is difficult to move to optimize its position in a given environment. In addition, it requires a phase of acquisition of at least one image, constituting an additional step that increases the duration of the method.

A simpler method consists for a spectacle wearer in taking hold of an apertured card or an equivalent object, and in looking at an identified point through the hole. An optometrist placed in front of said wearer focuses on his gaze in order to determine which is his dominant eye. Such a method remains approximate and particularly constraining for the wearer, who is obliged to perform a somewhat difficult manipulation of the sighting device i.e. the apertured card.

Sighting devices according to the invention allow a method for determining the dominant eye of a spectacle wearer to be carried out while avoiding the drawbacks of the prior art. In this way, a method for determining the dominant eye according to the invention is carried out ergonomically, practically and comfortably as regards the spectacle wearer, and may be implemented optimally in any type of environment, because it involves a simplified and not very bulky apparatus.

One subject of the invention is an apparatus for implementing a method for determining the dominant eye of a spectacle wearer, comprising a target, a means for occulting at least one eye, and a sighting device equipped with an optical window.

The principal feature of an apparatus according to the invention is that the sighting device comprises an electronic sensor making it possible to identify a movement of said sighting device, during said method during various steps of viewing the target. Such an apparatus makes it possible to obtain directly, by virtue of the electronic sensor, all the information characterizing a movement of the sighting device, such as the direction, amplitude and duration of the movement. It is assumed that the electronic sensor is connected, by a wire or wirelessly, to an integrated or external system for receiving and processing the signal emitted by said sensor, in order to evaluate the direction and the amplitude of the movement of the sighting device, during the viewing of the target through the optical window of the sighting device. Advantageously, the electronic sensor is a 3D sensor. This electronic sensor, which makes it possible to know directly the direction of movement and the position of the sighting device in space, may, for example, be of the magneto-gyroscopic type. Advantageously, said sensor is an accelerometer and/or inclinometer. The sighting device is an object that the wearer may take hold of with his hands and that he may orient as desired in space. An optical window is a limited aperture placed in the sighting device. There may be only one aperture and it may be of constant size. Its size may also be variable, for example by means of a sliding obturator.

Optionally, this aperture may be embodied by a glass slide, which will possibly be tinted or divided into quadrants. Such an aperture may be, either produced directly in the sighting device, or added to said sighting device by way of an added interface part. The target is an identifiable object able to be fastened against a wall or on the ground or to be placed on a table. This target may for example consist of an adhesive strip bearing a distinctive pattern. The means for occulting at least one eye, may consist of an object that is positioned directly on the face of the wearer, or by an object that is fastened to a spectacle frame. This occulting means may for example consist of an opaque shield that is placed in front of one eye in order to prevent it from seeing. It may be mechanical in nature and be controlled manually. It may also be electronic in nature, and be controlled automatically by way of a remote control.

Advantageously, the sighting device is a tablet, the electronic sensor being integrated into said tablet. This tablet may simply be a medium with a windowed shield, or be of the electronic type. In this second category, it may be equipped with a touchscreen. In the case where this tablet is of electronic origin, it may either have been specifically designed for taking measurements in the context of the definition of frames, or consist of an already existing mass-market tablet designed for various domestic uses, such as for example connecting to the Internet, taking photos and/or videos and executing various downloads. According to another possible configuration, the electronic sensor may be external to the tablet and be fastened thereto.

Preferably, the target has a central pattern and secondary patterns ordered so that viewing of the secondary patterns alone makes it possible to deduce in which direction the central pattern is located. In this way, a spectacle wearer who can see only the secondary patterns because of the occultation of one of his eyes will know directly in which direction to move the sighting device to observe the central pattern. The central pattern may advantageously be a simple geometric figure such as a circle, square, diamond or triangle. The secondary patterns may for example be chevrons, arrows or triangles.

Preferably, the target is foldable and may be stored in a compartment associated with the tablet. This target may for example consist of a plastic-coated card or a plastic strip. It may also have an adhesive face. The fact that it is foldable makes it possible for it to occupy a small volume and for it to be easily transported or stored.

Advantageously, the electronic sensor makes it possible to identify the sign, amplitude, direction, duration and the accelerations of the movements of the sighting device.

Advantageously, the tablet is an electronic tablet equipped with a camera and an optical window. This tablet may have been specifically designed to take measurements in the field of optics, in order to personalize a pair of corrective spectacles, or consist of a tablet developed for various applications such as connecting to the Internet and acquiring images. An additional camera may for example serve to determine a reading distance for a spectacle wearer. The optical window may feature in an added part intended to be fastened to the tablet.

Advantageously, an apparatus according to the invention comprises a tablet equipped with the electronic sensor and an operational kit able to be mounted on said tablet, said kit including at least one holding part, the optical window, the occulting means and the target, the holding part being intended to be mounted on the tablet in order to serve as a point for fastening the optical window. This kit incorporates all the elements required to determine the dominant eye. The holding part conforms to the tablet and serves as a base for fastening the optical window. If the occulting means is electronic, the kit also contains the remote control that serves to actuate said occulting means. According to one preferred embodiment of an apparatus according to the invention, the holding part of the kit is designed to serve as a case for transporting all the other constituent elements of said kit.

Preferably, the occulting means is electronic and is operated by means of a remote control. In this way, said means operates automatically on being controlled remotely, and a delicate manual intervention on the part of a third person, and which could possibly be considered intrusive by the spectacle wearer, is avoided.

Preferably, the tablet is equipped with locating markers provided for viewing said tablet in space. These markers may for example be mini chequerboards each comprising two white boxes and two black boxes. These inactive markers make it possible to easily and clearly pinpoint the position of the tablet in space, and especially in an image.

Advantageously, the electronic sensor is an inclinometer and/or a 3D accelerometer.

The second subject of the invention is a method for determining the dominant eye of a spectacle wearer by means of an apparatus according to the invention, characterized in that it comprises the following steps:

A first step in which the wearer views, with both eyes open, the target through the optical window of the sighting device, which he holds in his hand and the position of which he adjusts;

A second step of viewing said target with a single eye, selected with the occulting means, the wearer moving the sighting device if it proves to be necessary;

An optional third step of viewing said target with the other eye, selected with the occulting means, the wearer moving said sighting device if it proves to be necessary; and A fourth step of determining the dominant eye based on each movement of the sighting device detected by the electronic sensor.

In other words, once the wearer is viewing the target with both eyes open through the optical window, he freezes the sighting device in an appropriate first position. Next, an occulting means allows one eye then the other to be alternatively occulted in order to demonstrate the disappearance of the observed target, and to provoke if needs be a translational movement of the tablet in order to align the eye with the target.

In the second step, if the eye that is not dominant is occulted, the wearer will be able to see the target with his dominant eye through the optical window of the device, without having to significantly change the position of said sighting device. The third viewing step consists in occulting the other eye, which is in this case his dominant eye. Since he cannot see the target with his non-dominant eye, the wearer moves the sighting device significantly in order to view the target with said non-dominant eye.

If in the second step his dominant eye is occulted, he will not be able to see the target with his non-dominant eye. He then moves the sighting device significantly into a second position in order to see the target with his non-dominant eye. In the third step the non-dominant eye of the wearer is occulted in order to view the target with his dominant eye. In this situation, he cannot see the target with his dominant eye; the wearer moves the sighting device in order to view the target with said dominant eye.

The various movements, numbers, amplitudes and shapes of the signals of the sighting device during these steps are recorded by the electronic sensor and, in combination with the occulting information of a given eye, allow the dominant eye of the wearer to be defined. A statistical analysis optionally makes it possible to refine the result.

Advantageously the analysis of the signals makes it possible to provide a degree of confidence, which is more or less marked, in the dominant eye determined, which will be referred to as ocular predominance.

Advantageously, light-emitting diodes associated with the occulting means make it possible to guide the optician during the measurement process. For example, when the diode is flashing green the method is in the process of measuring. When the latter stops flashing the dominant eye has been detected. Lastly, when the diode is orange an error is detected, resulting either from an irregular movement or a movement that is too large.

Advantageously, if in the second step the wearer needed to move the sighting device in order to view the target in a second position, the method according to the invention comprises a first intermediate step comprised between the second and third steps, said first intermediate step consisting in repositioning said sighting device in the first position obtained in the first step, said repositioning constituting a movement that is detected by the electronic sensor.

If in the third step the wearer needed to move the sighting device in order to view the target in a third position, the method according to the invention comprises a second intermediate step comprised between the third and fourth steps, said second intermediate step consisting in repositioning said sighting device in the first position obtained in the first step, said repositioning constituting a movement that is detected by the electronic sensor.

The dominant eye may be measured in combination with the occulting means by counting the number of movements carried out with each eye occulted.

Preferably, the target has a central pattern and ordered secondary patterns making it possible to deduce in which direction the central pattern is located, and when the dominant eye is occulted in the second or third step the wearer knows in which direction he must move the sighting device in order to view the central pattern with his non-dominant eye. This type of target makes it possible to inform the wearer of the direction in which he must move the sighting device to view the central pattern with his non-dominant eye, when his dominant eye is occulted and he can see only the secondary patterns with his non-dominant eye.

Preferably, the second and third steps are each preceded by a step of actuating the occulting means, said occulting means being electronic and actuated remotely by means of a remote control.

Advantageously, the method comprises a step of presenting results by means of display of a photo showing the open eyes of the spectacle wearer and a visual indication in said photo of the dominant eye. Optionally, an indicator of the degree of ocular predominance of this dominant eye may also be displayed. This photo may appear, either on a computer screen, or on a paper medium.

Advantageously, the method comprises a step of determining an ocular predominance indicator.

Below, a detailed description of one preferred embodiment of an apparatus and method for determining dominant eye according to the invention is given with reference to FIGS. 1 to 6C.

FIG. 1A is a front view of a spectacle wearer equipped with a manual means for occulting at least one of his eyes and belonging to an apparatus according to the invention, the left eye of said wearer being occulted;

FIG. 1B is a front view of a spectacle wearer equipped with a manual means for occulting at least one of his eyes and belonging to an apparatus according to the invention, the right eye of said wearer being occulted;

FIG. 2 is a front view of an electronic means for occulting at least one of the eyes of the wearer and belonging to an apparatus according to the invention;

FIG. 3 is a target of an apparatus according to the invention;

FIG. 4A is a perspective view of a tablet of an apparatus according to the invention equipped with an optical window;

FIG. 4B is a kit comprising elements of an apparatus according to the invention;

FIGS. 5A, 5B and 5C show front views of an individual looking at a target through the optical window of a tablet, with both eyes open, with his right eye occulted and then with his left eye occulted, respectively, said views showing the three main steps of a method according to the invention; and FIG. 6 illustrates an exemplary record of the signal emitted by the 3D sensor, during a method according to the invention.

An apparatus for implementing a method for determining the dominant eye of a spectacle wearer 1 comprises a target 2, a means 3, 4 for occulting at least one eye of said wearer 1, and a tablet 5, 50 equipped with an optical window 6 and a 3D electronic sensor of the magneto-gyroscopic type. Said sensor is connected to a processor integrated into the tablet, which processor is equipped with a signal-processing module in particular making it possible to evaluate the sign, amplitude, direction, duration and accelerations of the movements of the tablet 5, 50 during the various steps of a method for determining the dominant eye according to the invention.

Preferably, a single one axis X of the 3D electronic sensor fastened to the tablet 5, 50, corresponding to the axis X of horizontal movement of said tablet 5, 50, is preferred for the measurements. For example, a measurement of the acceleration of the tablet 5, 50 along the horizontal axis X is recorded every 41 ms over a range extending from −4 g to +4 g. The measurements are signed and thus allow from the recorded signal the direction of movement of the tablet 5, 50 to be evaluated. In order to remove the slight noise in the signal, related to natural, very small amplitude movements of the wearer and/or the non-horizontality of the tablet 5, 50, before each measurement phase the average value of the signal is determined and saved, then subtracted from subsequent measurements.

For each movement of the tablet 5, 50 the process evaluates, from the signal, peak-to-peak values between the minimum and maximum amplitudes of the movements, and the distribution of the peaks, in order to differentiate a significant movement of the tablet related to the dominant-eye measurement protocol from an absence of movement. A very slow movement is equated to an absence of movement. For example, a peak-to-peak amplitude smaller than an acceleration threshold of 0.02 g is considered as an absence of movement. A movement associated with an acceleration higher than the latter threshold is considered as having a significant acceleration. This threshold may be adjusted depending on the type of population. Specifically, this threshold value will be higher for an elderly population than for a younger population. Likewise, this threshold value will be higher for an active person than for a sedentary person.

With reference to FIGS. 1A and 1B, the occulting means 3 may be two opaque shutters 7 able to be placed over the lenses of a spectacle frame. In FIG. 1A, an optician 8 has placed such a shutter 7 over the left lens of the wearer 1, so that only his right eye can see. In FIG. 1B, the optician 8 has placed the shutter 7 over the right eye so that only the left eye of the wearer can see. Generally, the shutters 7 are used only to occult a single eye at a time.

With reference to FIG. 2, the occulting means 4 is electronic and may be automatically controlled remotely by way of a remote control. The occulting means 4 takes the form of a mask 9 intended to cover the two lenses of a frame, said mask 9 being equipped with two apertures each of which is able to be obturated by an opaque shutter 10, independently one from the other. The distance separating the two apertures corresponds approximately to the distance separating the two eyes of the wearer 1. Thus, on actuation with the remote control, each shutter 10 may slide autonomously in the mask 9, either to obturate an aperture, or to free said aperture if it was obturated beforehand. The mask 9 has a central notch 11 in order to allow the nose of the wearer 1 to pass, and a series of three markers 12, 13 each embodied by a mini chequerboard comprising four boxes two of which are black and the other two of which are white. These three markers 12, 13 are aligned in a direction parallel to an axis connecting the two apertures, one marker 13 being in a central position on the mask 9 level with said notch 11, and the other two markers 12 being in lateral positions. Such an occulting means 4 may also comprise at least one signaling light-emitting diode 14 allowing the optician to be informed of the state of progress of the method for determining the dominant eye according to the invention.

With reference to FIG. 3, an apparatus according to the invention comprises an elongate target 2 taking the form of a rectangular strip possessing a central square 15 surrounded by triangles 16 pointing toward said central square 15. Specifically, on either side of the central square 15, the target 2 comprises a series of regularly spaced triangles 16, each of said triangles 16 having an apex oriented in the direction of the central square 15. The two series of triangles placed around the central square may be different colors. These triangles act as guiding elements indicating the location of the central square 15. In this way, a wearer 1 who is able to see only one series of triangles 16, because one of his eyes is occulted, will know directly in which direction he must move the tablet 5, 50 in order to view the central square 16 with his other eye. The target 2 is for example placed at about 3 m from the wearer 1, either on the ground or on a table.

With reference to FIG. 4A, the tablet 5 may be an already existing mass-market electronic tablet developed especially in order to allow access to the Internet, to make it possible to take photos or videos and to carry out various downloads.

These tablets 5 are generally of small thickness and possess a touchscreen 17 encircled by a rectangular frame 18. They already comprise an integrated 3D electronic sensor, but are devoid of optical window 6. It will be noted that an optical window 6 is characterized by a limited aperture, possibly occupied by a transparent glass slide, and through which the wearer 1 will be able to look at the target 2. For this type of tablet 5, an apparatus according to the invention provides a receiving part 19 and a sighting part 20 equipped with the optical window 6 and able to be inserted into said receiving part 19. The receiving part 19, which comprises a slit 21, is placed easily and rapidly on one edge of the tablet 5, then the sighting part 20 is subsequently inserted into said slit 21 in such a way as to make the optical window 6 emerge from said tablet 5.

With reference to FIG. 4B, the apparatus according to the invention provides a complete kit 22 for mounting on an already existing electronic tablet 5 in order to allow a method for determining the dominant eye according to the invention to be carried out. This mounting kit 22 possesses a compartmentalized central holding part 23 one lodging 24 of which is provided for the sighting part 20 equipped with the optical window 6, another lodging of which 25 is provided for the electronic occulting means 4, and another lodging of which 26 is provided for the remote control 27 of said occulting means 4. An additional compartment (not shown in the figure) is reserved for the foldable target 2.

With reference to FIGS. 5A to 5C, according to a second preferred embodiment of an apparatus according to the invention, the tablet 50 may consist of a tablet analogous to the one that is, for example, described in patent application FR2972339. This tablet 50 possesses an integrated optical window 6 and may hold a readable text. Chequerboard markers positioned on the back of the tablet 50 make it possible to pinpoint the position of said tablet in space, and therefore in an image. Such a tablet 50, in addition to making it possible to determine the dominant eye of the wearer 1, also allows a reading distance to be evaluated by means of an exterior image acquisition system.

With reference to FIGS. 5A to 5C, a method for determining the dominant eye of a spectacle wearer by means of an apparatus according to the invention comprises the following steps:

A first step in which the wearer 1 views, with both eyes open, the target 2 through the optical window 6 of the tablet 5, 50, which he holds in his hand and the position of which he adjusts, as shown in FIG. 5A. Once the wearer 1 is looking at the target 2, the tablet 5, 50 is considered to occupy a first reference position. This first reference position is determined by the dominant eye of the wearer, which is not occulted at this stage.

A second step in which the wearer 1 views said target 2 only for example with his left eye, the occulting means 3, 4 being adjusted so that the right eye is obturated in the first reference position. If the wearer 1 possesses a dominant right eye, then he will have to move the tablet 5, 50 laterally to a second position in order to be able to view the central square 15 of the target 2 with his left eye. The 3D sensor will then detect a first lateral acceleration of said tablet 5, 50. To help the wearer more easily locate the position of the target 2, the direction in which the wearer 1 must move the tablet 5, 50 will be directly indicated by the triangles 16 of the target 2 surrounding the central square 15, which the wearer 1 views with his left eye. If the wearer 1 possesses a dominant left eye, he will then be able to view the central square 15 of the target 2 in this step directly, without having to move the tablet 5, 50. In this case, the 3D sensor does not record a signal bearing witness to a significant acceleration of said tablet 5, 50.

A third step in which the wearer 1 views said target 2 only with his right eye, the occulting means 3, 4 being adjusted so that his left eye is obturated. If the wearer possesses a dominant right eye, he will have to reposition the tablet 5, 50, which he moved beforehand in the second step, to a third position corresponding to a viewing position of the central square 15 of the target 2 with both eyes open. The 3D sensor will then record an acceleration corresponding to the repositioning of the tablet 5, 50. If the wearer possesses a dominant left eye, he will move the tablet 5, 50 laterally in order to be able to view the center 15 of the target 2 with his non-dominant eye. The 3D sensor will then record an acceleration related to the movement of said tablet 5, 50. The third position may correspond substantially to the first position.

With reference to FIG. 6, with a method carried out according to the above protocol, if the wearer 1 possesses a dominant right eye, the 3D sensor will record two horizontal movements along X of the tablet 5, 50, one in order to allow the center 15 of the target 2 to be observed with the left eye of the wearer, corresponding to the movement of the tablet from the first position to the second position, and the other in order to position the tablet 5, 50 from the second position to the third position. If he possesses a dominant left eye, the 3D sensor will record only a single movement of the tablet 5, 50. The curve 28 representative of a movement of the tablet 5, 50 along a horizontal axis X, clearly shows two peaks 29, 30 corresponding to two movements of the tablet 5, 50, which are required if the wearer possesses a dominant right eye. In order to confirm the diagnosis, the sequence of the three steps of the method may be repeated a plurality of times over time. It will be noted that the axis Y corresponds to a vertical axis and the axis Z is a depth axis corresponding to how far or close the tablet is to the individual and which is substantially orthogonal to the X and Y axes, and that the movement of the tablet 5, 50 along these two axes is negligible.

Advantageously, a simplified system may be obtained with a preset table programmed into the processor, said table making it possible, depending on the eye occulted in the first step, to determine which is the dominant eye merely from whether an acceleration peak is detected or not in the second step. Thus, the eye occulted in the first step is entered by way of a declarative manual means such as an input or a synchronized acquisition of images followed by image processing, or, if an automatic system for determining the occulted eye is available, using an electronic occulting system.

For example, if the right eye is occulted and a significant peak is detected in the second step then the dominant eye is the right eye. If no significant peak is detected, the dominant eye is the left eye. In contrast, if the left eye is occulted in the first step and a significant peak is detected in the second step, the dominant eye is the left eye, otherwise it is the right eye that is dominant. A peak is considered to be significant if it is higher than a preset threshold, for example, positioned for a peak-to-peak amplitude of the peak corresponding to an acceleration of 0.02 g.

However, the measurements carried out in the third phase are preferable and will allow the result to be refined, by detecting anomalies and verifying the consistency of the data.

In one dominant-eye measurement cycle a plurality of pieces of information regarding the 2 portions of the measurement are captured and saved, one corresponding to the right eye and the other to the left eye:

The maximum positive acceleration;
The minimum negative acceleration; and
The distribution of the movement peaks represented in a histogram.

The distribution of the peaks corresponds to a tiered classification of samples by magnitude. For example, we will consider 11 tiers for characterizing the signal, with each tier corresponding to an acceleration of 0.01 g each for the 10 first tiers (0->10, 11->20, 21->30, etc.) and for the 11th tier to values higher than 100 mg.

The two first tiers correspond to micro-movements or the absence of movement due to the person trembling, and represent an acceleration lower than 0.02 g. This absence of movement will be represented by a large number of samples in the first tier, few in the second tier, and none in the following tiers.

A movement of normal speed typically generates a few peaks in the tiers of number higher than or equal to three, and many samples in the two first tiers of magnitude.

After the phase of acquisition of the movements, an analysis is carried out on the various portions of the signal in order to determine whether the measurement is valid or if it must be rejected due to a movement being irregular or indeed characterized by a large amount of measurement noise or even by an absence of movement.

To do this various "types of noise" are identified in a prior calibration phase in which the thresholds are set depending on the conditions of use and the individual. In these cases, the movement is considered to be incorrect and an alarm is presented to the operator in order optionally to restart the method.

If intermediate tiers three and four each for example contain more than 5 samples, this is considered to be too much movement in tiers of low values and is therefore equated to a moderate amount of shaking.

If the six last tiers of the distribution contain in total more than 5 samples, then this is considered to be too much movement in the high tiers and equated to an abnormal movement such as, for example, a movement that is too jerky or without stabilization on the dominant eye.

If the signal is considered valid, then the calculation of the dominant eye seeks to detect a movement in each portion of the measurement corresponding to the second and third steps of the method.

A nocular predominance indicator corresponding to a degree of confidence, which is more or less marked, in the dominant eye determined is presented. This indicator provides an additional aid to the optician when characterizing the dominant eye of the individual. The ocular predominance may be marked, low or normal. This indicator is evaluated on the basis of a cycle corresponding to the second and third steps.

The analog dominance value is for example characterized by temporal analysis of the signals and obtained by the ratio $D=TS/(TR+TS)$, where TR: is the average reaction time following occultation; and
TS: is the average stabilization time after movement.

Typical values are 0.8 to 1.6 s for TR and 0.8 to 2 s for TS. These values are conventionally adjusted by an empirical curve and by experience.

| | magnitude (IS) mg | ratio (RS) signal 1/s2 | reaction (TR) second | stabilization (TS) second |
|---|---|---|---|---|
| | typical values | | | |
| high | >150 | >4 | <0.8 | <0.8 |
| normal | 100-150 | 3 | 0.8-1.6 | 0.8-2 |
| low | 60-100 | 2 | >1.6 | >2 |
| | Dominance D = IS * (1 + RS/10)/ (TR + TS)/2 | | | |
| low | < | 70 | | |
| normal | >70 | <250 | | |
| marked | > | 260 | | |

Thus, if the ratio is lower than 30% the predominance indicator will be low, if it is comprised between 30 and 60% it will be considered as normal, and it will be considered as marked for a ratio higher than 60%.

A method according to the invention comprises a fourth step of presenting results by means of display of a photo, showing the open eyes of the spectacle wearer 1, and a visual indication in said photo allowing the dominant eye to be identified.

Optionally, the light-emitting diode 14 of the electronic occulting means 4 will be used to guide an optician through the method. For example:

When said diode 14 is flashing green, the measurement is being carried out and the dominant eye has not yet been detected;

When said diode 14 stops flashing the dominant eye has been detected;

When said diode 14 is flashing orange, initialization of the measurement is in progress; and Lastly, when said diode 14 is continuously orange, the measurement has been carried out.

The invention claimed is:

1. An apparatus for implementing a method for determining the dominant eye of a spectacle wearer (1), comprising a target (2), a means (3, 4) for occulting at least one eye, and a sighting device (5, 50) equipped with an optical window (6), wherein the sighting device (5, 50) comprises an electronic sensor making it possible to identify a movement of said sighting device (5, 50), during said method during various steps of viewing the target (2).

2. The apparatus as claimed in claim 1, wherein the sighting device is a tablet (5, 50), and the electronic sensor is integrated into said tablet (5, 50).

3. The apparatus as claimed in claim 2, wherein the target (2) has a central pattern (15) and secondary patterns (16) ordered so that viewing of the secondary patterns (16) alone makes it possible to deduce in which direction the central pattern (15) is located.

4. The apparatus as claimed in claim 3, wherein the tablet is an electronic tablet (5) equipped with a camera and an optical window (6).

5. The apparatus as claimed in claim 3, further comprising a tablet (5, 50) equipped with the electronic sensor and an operational kit able to be mounted on said tablet (5, 50), and said kit includes at least one holding part (19), the optical window (6, 20), the occulting means (3, 4) and the target (2), the holding part (19) being intended to be mounted on the tablet (5, 50) in order to serve as a point for fastening the optical window (6, 20).

6. The apparatus as claimed in claim 2, wherein the tablet is an electronic tablet (5) equipped with a camera and an optical window (6).

7. The apparatus as claimed in claim 2, further comprising a tablet (5, 50) equipped with the electronic sensor and an operational kit able to be mounted on said tablet (5, 50), and said kit includes at least one holding part (19), the optical window (6, 20), the occulting means (3, 4) and the target (2), the holding part (19) being intended to be mounted on the tablet (5, 50) in order to serve as a point for fastening the optical window (6, 20).

8. The apparatus as claimed in claim 1, wherein said electronic sensor makes it possible to identify the sign, amplitude, direction, duration and the accelerations of the movements of the sighting device (5, 50).

9. The apparatus as claimed in claim 1, wherein the occulting means (4) is electronic and is operated by means of a remote control (27).

10. The apparatus as claimed in claim 1, wherein the tablet (5, 50) is equipped with locating markers provided for viewing said tablet (5, 50) in space.

11. The apparatus as claimed in claim 1, wherein the electronic sensor is an inclinometer and/or a 3D accelerometer.

12. A method for determining the dominant eye of a spectacle wearer by means of an apparatus as claimed in claim 1, wherein the method comprises the following steps:
- A first step in which the wearer (1) views, with both eyes open, the target (2) through the optical window (6) of the sighting device (5, 50), which he holds in his hand and the position of which he adjusts;
- A second step of viewing said target (2) with a single eye, selected with the occulting means (3, 4), the wearer (1) moving the sighting device (5, 50) if it proves to be necessary;
- An optional third step of viewing said target (2) with the other eye, selected with the occulting means (3, 4), the wearer (1) moving said sighting device (5, 50) if it proves to be necessary; and
- A fourth step of determining the dominant eye based on each movement of the sighting device (5, 50) detected by the electronic sensor.

13. The method as claimed in claim 12, wherein, if in the second step the wearer (1) needed to move the sighting device (5, 50) in order to view the target (2) in a second position, said method comprises a first intermediate step comprised between the second and third steps, said first intermediate step consisting in repositioning said sighting device (5, 50) in the first position obtained in the first step, said repositioning constituting a movement that is detected by the electronic sensor.

14. The method as claimed in claim 13, wherein the target (2) has a central pattern (15) and ordered secondary patterns (16) making it possible to deduce in which direction the central pattern (15) is located, and when the dominant eye is occulted in the second or third step the wearer (1) knows in which direction he must move the sighting device (5, 50) in order to view the central pattern (15) with his non-dominant eye.

15. The method as claimed in claim 13, wherein the second and third steps are each preceded by a step of actuating the occulting means (3, 4), and said occulting means (4) is electronic and actuated remotely by means of a remote control (27).

16. The method as claimed in claim 13, further comprising step of presenting results by means of display of a photo showing the open eyes of the spectacle wearer (1) and a visual indication in said photo of the dominant eye.

17. The method as claimed in claim 13, further comprising a step of determining an ocular predominance indicator.

18. The method as claimed in claim 12, wherein the second and third steps are each preceded by a step of actuating the occulting means (3, 4), and said occulting means (4) is electronic and actuated remotely by means of a remote control (27).

19. The method as claimed in claim 12, further comprising a step of presenting results by means of display of a photo showing the open eyes of the spectacle wearer (1) and a visual indication in said photo of the dominant eye.

20. The method as claimed in claim 12, further comprising a step of determining an ocular predominance indicator.

\* \* \* \* \*